United States Patent [19]

Urbaniak

[11] Patent Number: 4,465,472
[45] Date of Patent: Aug. 14, 1984

[54] SYRINGE CARTRIDGE AND METHOD
[75] Inventor: Ray Urbaniak, Boca Raton, Fla.
[73] Assignee: American Hospital Supply Corp., Evanston, Ill.
[21] Appl. No.: 443,647
[22] Filed: Nov. 22, 1982
[51] Int. Cl.³ .............................................. A61M 1/00
[52] U.S. Cl. .................................... 604/122; 604/187; 128/763
[58] Field of Search ................ 604/122, 124, 125, 187, 604/240, 263, 416, 229, 199–205; 128/763, 765, 767; 141/27

[56] References Cited

U.S. PATENT DOCUMENTS

| | | | |
|---|---|---|---|
| 1,707,880 | 4/1929 | Sheets | 604/125 |
| 4,044,758 | 8/1977 | Patel | 604/125 |
| 4,057,050 | 11/1977 | Sarstedt | 604/125 |
| 4,289,648 | 9/1981 | Hoskins et al. | 604/416 X |
| 4,291,701 | 9/1981 | Bowman | 604/122 |

Primary Examiner—John D. Yasko
Attorney, Agent, or Firm—Jack E. Dominik; John H. Faro

[57] ABSTRACT

Disclosed is a method for filling a cartridge which can be subsequently capped and closed. This is done by filling to a discrete level and then applying a closure. A displacement dome is provided at the lower portion of the syringe cartridge closure to first displace a predetermined amount of air or gas and then to displace a minor amount of fluid upon closure to seal the cartridge, and insure zero head space. The entirety of the process of filling is done in a vented environment, and the closure applied at ambient. The invention also provides an apparatus which includes a syringe cartridge having its open lower portion closed by a plunger piston. The upper portion is closed by a syringe cartridge closure having a leur tip cap. Means are optionally provided interiorly of the tip cap to retain a hollow needle, which is held in position by a leur tip, the latter being vented and provided with a seal for the needle. The piston plunger at the lower portion of the cartridge can be advanced, desirably by a second plunger, to empty the contents. Upon resealing, the leur tip cap is applied over the leur tip after a bead is formed on the tip. The tip cap then penetrates the leur tip, or optionally the interior of the hollow needle thus completely reclosing the cartridge and sealing the same for storage until intended for further use.

14 Claims, 20 Drawing Figures

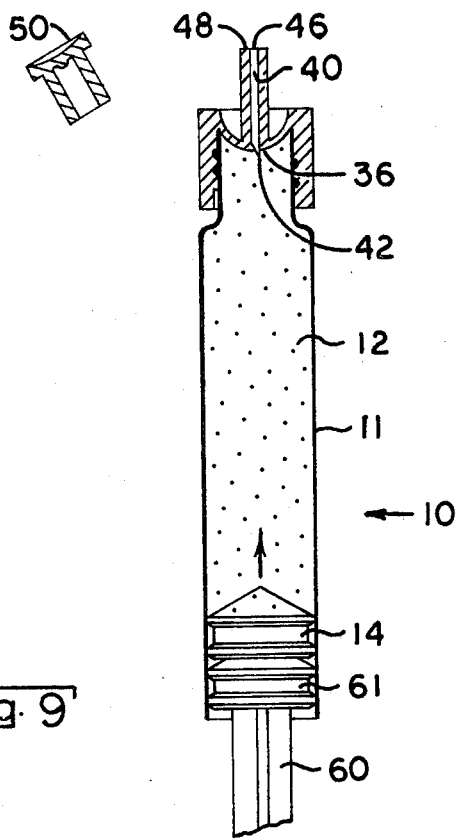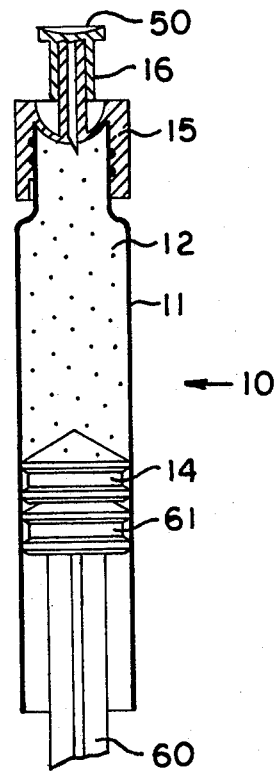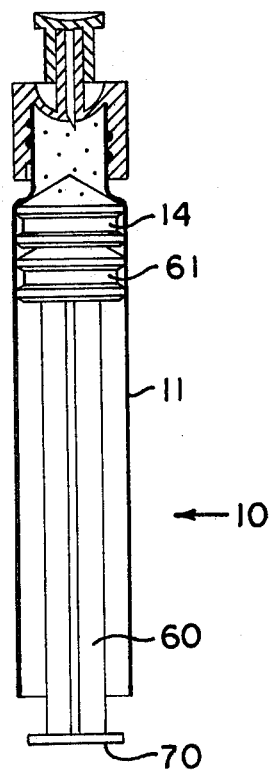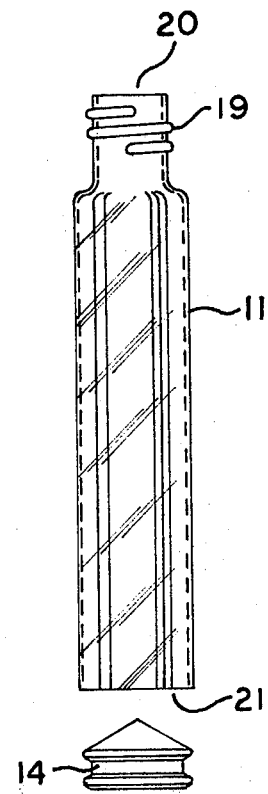

SYRINGE CARTRIDGE AND METHOD

FIELD OF INVENTION

The present invention is directed to a syringe cartridge, and method for filling and dispensing from the same, which provides for controlled or zero head clearance with the contents, thereby isolating the contents from ambient air.

SUMMARY OF THE PRIOR ART

Measurement of human blood gases is a well known medical test and is routinely performed with specialized blood gas instruments. These instruments must be frequently tested for accuracy and calibration to insure that reliable measurements are being made. Recently the advantages of using gas-equilibrated, buffered, stabilized human blood cell suspensions as quality control specimens to be run in conjunction with patient specimens have been described. See for example U.S. Pat. No. 4,126,575 to Louderback. However, such blood gas control material requires special handling, including incubation and agitation prior to use, and avoidance of contact with air.

An attempt was made by Intensive Technology, Inc. of 25 Bay State Road, Boston, Mass., in a product called "Respatrol" to minimize the above problems by sealing the blood gas control with a gel. However, the integrity of the seals as well as opening and resealing of the ampules was less than satisfactory.

It thus becomes highly desirable, in view of the prior art and the problems, to provide for zero head space in a cartridge, and continuing zero head space during the dispensing of the contents of the cartridge, particularly where whole blood or other ingredients are involved that must be sealed from ambient air. It further becomes highly desirable to accomplish such a packaging with resealable and reclosure features which constantly inhibit the ingress of air into the container. Furthermore it is desirable to be able to dispense the entire contents without contamination by air after repeated usage and resealing.

SUMMARY OF THE INVENTION

The present invention is directed to a method for filling a cartridge which can be subsequently capped and closed. This is done by filling to a discrete level and then applying a closure. The closure bottom displaces a predetermined amount of air or gas and a small amount of product from the interior of the cartridge. The entirety of the process of filling is done in a vented environment, and the closure applied at ambient. The invention also provides an apparatus which includes a syringe cartridge having its open lower portion closed by a plunger piston. The upper portion is closed by a syringe cartridge closure having a leur tip cap. Means are optionally provided interiorly of the tip cap to retain a hollow needle, which is held in position by a leur tip, the latter being vented and provided with a seal for the needle. A displacement dome is provided at the lower portion of the syringe cartridge closure to displace a minor amount of fluid upon closure to seal the cartridge, and insure zero head space. The piston plunger at the lower portion of the cartridge can be advanced, desirably by a second plunger, to empty the contents. Upon resealing, the leur tip cap is applied over the leur tip after a bead is formed on the tip. The tip cap then penetrates the leur tip, or optionally the interior of the hollow needle thus completely reclosing the cartridge and sealing the same for storage until intended for further use.

In view of the foregoing it is a principal object of the present invention to provide a syringe cartridge with zero head space in the interior to eliminate ambient air. A related advantage stems from the use of the subject product with a whole blood control so that equilibration is not required.

Still another object of the present invention is to provide a syringe cartridge which permits continued re-use without contaminating the remaining contents.

Still another object of the present invention is to provide for a needle interiorly of the leur tip which is partially driven through the plastic membrane of the closure, to thus avoid plugging the needle due to coring of the needle opening.

Yet another object of the present invention is to minimize the force required to drive the needle by providing seal ribs interiorly of the leur tip, and yet retain the sealing function required to inhibit leakage around the needle.

A further object of the invention is to provide a syringe cartridge which is adaptable to utilization directly as a syringe by applying a hypodermic needle on the leur tip.

Still another important object of the present invention is to provide a method for packaging the contents into a syringe cartridge which is simple and efficient, and inhibits contamination of the contents from ambient air.

Another objective is to prepare a syringe cartridge and method for using the same which can be used with a wide variety of chemicals and reagents where controlled or zero head space is required to maintain the stability and activity of the contents.

BRIEF DESCRIPTION OF THE DRAWINGS

Further objects and advantages of the present invention will become apparent as the following description of an illustrative embodiment and method proceeds, taken in conjunction with the accompanying drawings, in which:

FIG. 9 is the next sequential view of the user showing the leur tip cap being removed, and pressure applied to the plunger piston and plunger shaft to dispense the contents of the cartridge;

FIG. 10 shows a further sequential view in which the leur tip cap is placed in position on the needle and the leur tip, thus sealing the same for storage and re-use;

FIG. 11 shows the condition of the cartridge and contents after the syringe or cartridge is virtually depleted of its contents, and the upper piston can no longer function;

FIG. 12 is a front elevation of the syringe cartridge;

DESCRIPTION OF THE PREFERRED EMBODIMENTS

Figure 1:
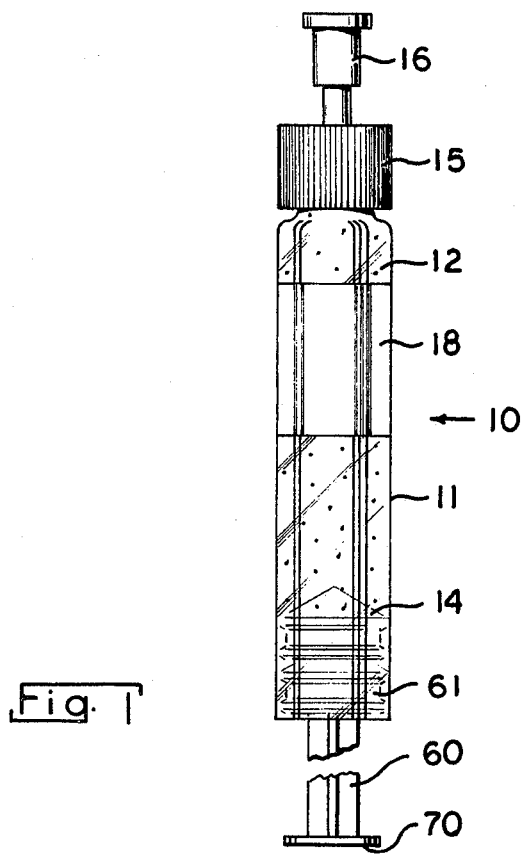
FIG. 1 is a front elevation of an illustrative syringe cartridge showing its principal elements as the product is sold to a typical user.

The subject syringe cartridge is shown in FIG. 1, where it will be seen that it has an elongated cartridge body 11, and filled with contents 12. A plunger piston 14 seals off the lower portion of the cartridge 11, and a syringe cartridge closure 15 is provided at the top. The syringe cartridge closure 15 has a leur tip cap assembly 16 which completes the closure. Conveniently shown is a typical wrap around label 18.

Figure 2:
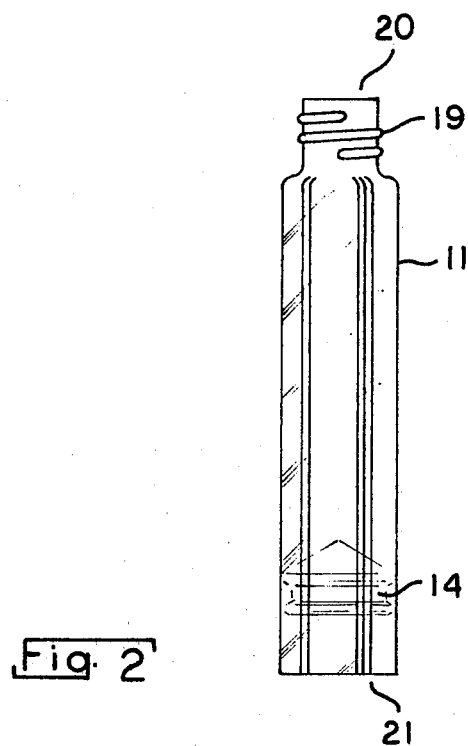
FIG. 2 is a front elevation in essentially the same scale as FIG. 1 showing the cartridge in its initial position prior to filling.

Turning to FIG. 2, it will be seen that the first step in assembling the syringe cartridge 10 is to provide a cartridge 11, preferably a sterilized glass tubular member, with the plunger piston 14 in place. To be noted is the upper portion of the cartridge 11 is provided with a thread finish 19, terminating in an open filling end.

Figure 3:
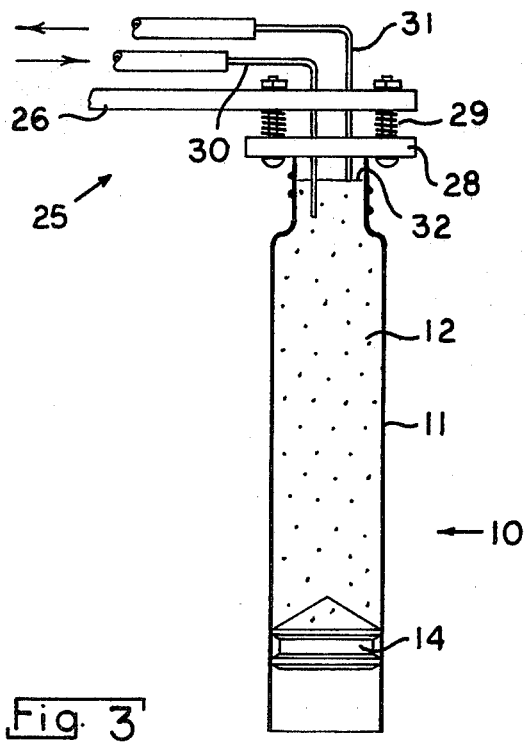
FIG. 3 shows the cartridge with its filling station as the same is being filled.

The next step illustrated in FIG. 3 is to fill the cartridge 11 with contents 12 in a drawback system. This is accomplished essentially by providing a filler head assembly 25 having a support bar or filler bar 26, and a cartridge cover 28 supported by a spring loaded suspension 29 from the filler support bar 26. A contents tube 30 is provided to penetrate through the cartridge cover 28 and dispense contents 12 into the cartridge 11. At the same time, a vent tube 31 is employed to permit the ambient atmosphere and excess product inside the cartridge 11 to be dispelled as the contents 12 are inserted. Pragmatically as well as theoretically, a precise controlled fill level 32 is calculated so that when the syringe cartridge closure 15 is applied, there will be an essentially total head space displacement, and the interior portion of the cartridge 11 will be solely occupied by its contents 12.

Figure 4:
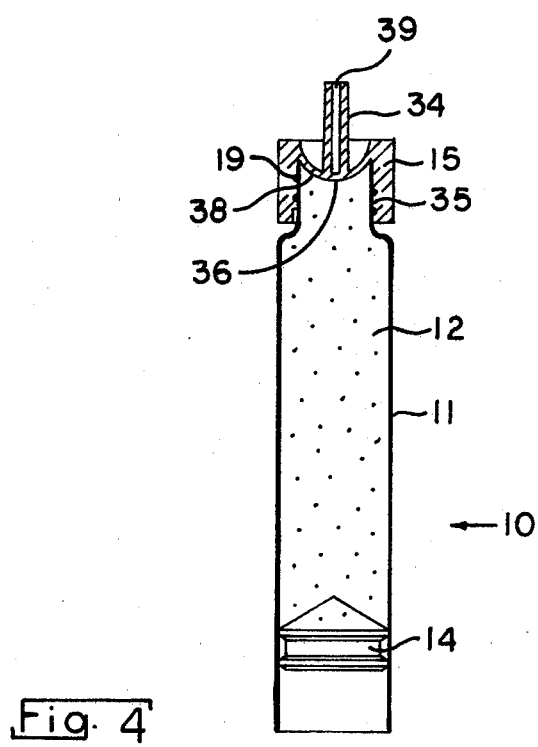
FIG. 4 discloses the filled cartridge after being filled in accordance with FIG. 3 and having the closure applied.
Figure 5:
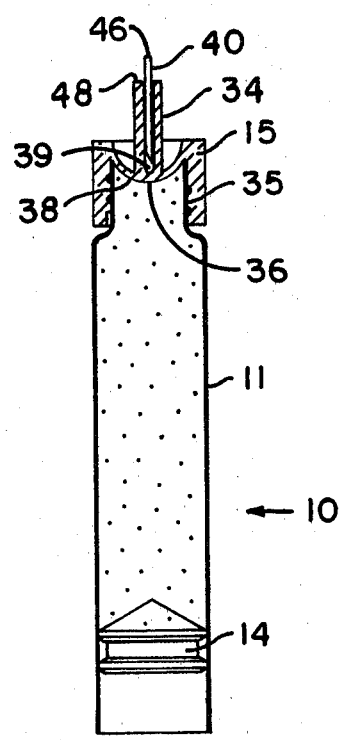
FIG. 5 discloses the next sequence in which the needle is inserted into the leur tip.

As shown in FIG. 4, when the closure 15 is applied to the threaded finish 19 of the cartridge 11, there is an observable leur tip 34, at the bottom of which is a diaphragm 36, from which extends the dome of the content displacement portion of the closure 15. The leur tip 34 also defines a leur tip needle bore 39 in its interior portion. The threaded finish 19 of the bottle along with the interior threads of the closure 15 form a contents displacement trap, which will become apparent as the closure 15 is subsequently described in greater detail along with drawings of more specific details. In closing the contents displacement trap 35 a small amount of the contents 12 will spill over but be trapped at the threaded joints between the closure 15 and the threaded finish 19 of the upper portion of the cartridge.

Figure 6:
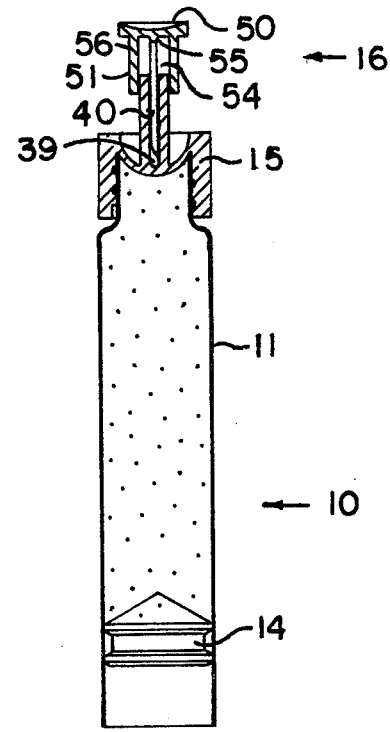
FIG. 6 is a further sequential view in which the leur tip cap is applied to the cartridge.
Figure 7:
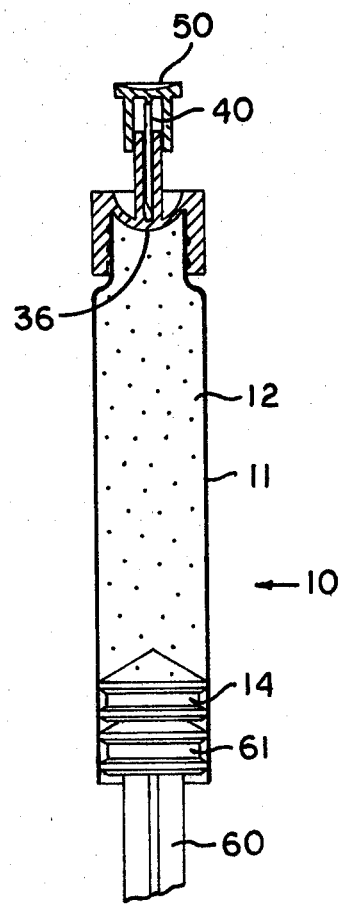
FIG. 7 shows the first step in preparing the cartridge for usage by inserting preferably a second shaft piston and plunger, and the same is now ready for shipment to the customer.
Figure 8:
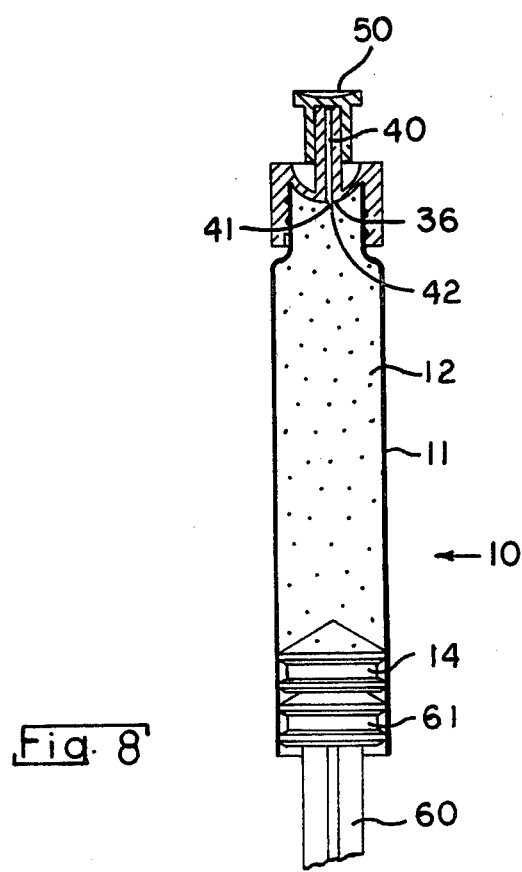
FIG. 8 shows the second step in which the leur tip cap is depressed, and the needle penetrates a diaphragm providing open communication with the contents of the cartridge.
Figure 18:
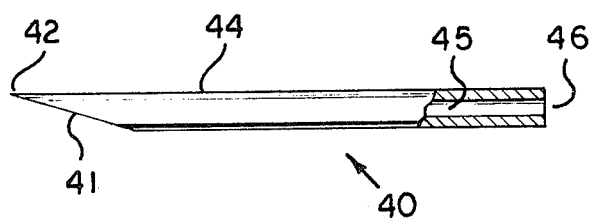
FIG. 18 is a front elevation of the needle in enlarged scale and showing its principal components.

As shown in FIG. 6, a hollow needle 40 is subsequently inserted into the leur tip needle bore 39. The needle 40, as shown in specific detail on FIG. 18, shows the termination at one end with a bevel 41 defining a point 42. The shank 44 of the needle contains a bore 45 which terminates at the dispensing end 46 of the needle 40. The opposite end of the bore 45 terminates at the bevel face 41 where the point 42 is defined. As will be shown, the leur tip dispensing end 48 is substantially flush with the needle dispensing end 46 when the unit is activated. FIG. 7 shows the insertion of the shaft piston 61 secured to the plunger shaft 60. The point 42 penetrates the diaphragm 36 (as shown in FIG. 8) but the bevel 41 only partially penetrates the diaphragm 36 to reduce any tendency for coring which would plug the needle 40.

Referring now to FIG. 9, after the needle 40 has been pressed into the contents and the tip 42 has penetrated the diaphragm 36 and is in contact with the contents 12 of the cartridge 11, the leur tip cap 50 is removed. Pressure is applied to the plunger 14, and the product then injected in accordance with the particular control coupler required. Alternatively the product can be dispensed into an intermediate container to be later drawn into the aspirating instrument. Upon conclusion of the dispensing, a small bead of contents 12 is formed at the top of the needle dispensing end 46 flush with the dispensing end 48 of the leur tip. Thereafter, as shown in FIG. 10, the technician replaces the leur tip cap and the syringe cartridge 10 is ready for storage until it is to be reused again. Finally, as shown in FIG. 11, the plunger piston 14 ultimately reaches a point in the neck of the cartridge 11 where no more contents can be dispelled, and the syringe cartridge and its contents are ready for disposal.

In greater detail, it will be seen in FIG. 12, that the syringe cartridge 11 has a thread finish 19 at one end, which is the filling end 20. The opposite plunger end 21 is left open and receives the plunger 14.

Figure 13:
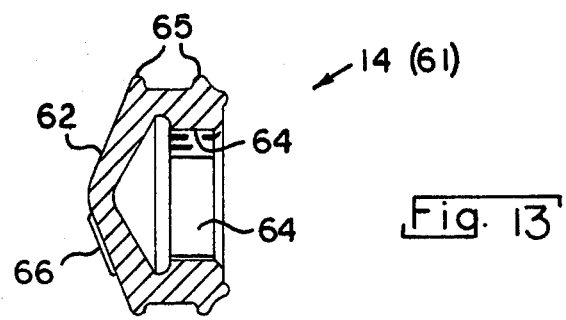
FIG. 13 is a transverse sectional view of the plunger piston.

In FIG. 13 the plunger piston 14 is shown having a dome 62. Interiorly a piston shaft lock colar 64 is provided to receive the piston shaft which will be described later. Exteriorly, a pair of seal rings 65 are shown which engage the interior wall of the cartridge 11. Optionally the dome 62 may be provided with ribs 66 which can serve to strengthen, as well as separate the plunger piston 14 from the second piston.

Figure 14:
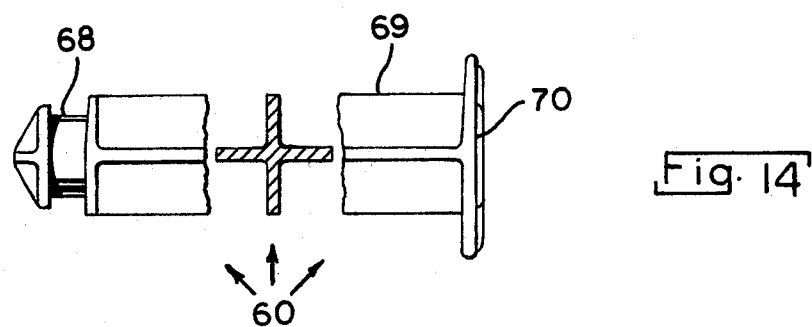
FIG. 14 is a front elevation partially in section of the plunger shaft.

Turning now to FIG. 14, the basic structure of the plunger shaft 60 is shown, and more specifically the connector head 68 which couples with the lock colar 64 of the plunger piston 14. The body 69 separates the connector head 68 from the thumb plate 70, which is used by the technician to activate the displacement of the contents 12 from the cartridge 11.

Figure 15:
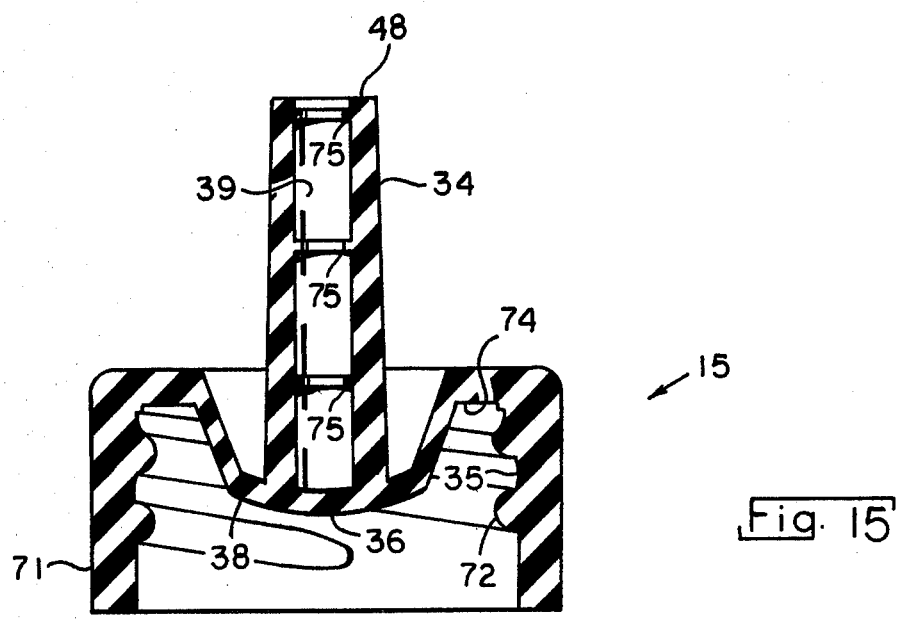
FIG. 15 is a transverse sectional view of the syringe cartridge closure.

The syringe cartridge closure 15 is shown in detail in FIG. 15. There it will be seen that the upper portion of the leur tip 34 terminates in a dispensing end 48. The leur tip 34 has an interior leur tip bore 39. The dome for product displacement 38 is shown at the bottom of the leur tip 34, and centrally it will be seen that a diaphragm 36 is provided for penetration by a needle 40. The contents displacement trap 35 is defined by the interior threads 72 of the skirt 71 which terminate in a seal at the interior of the upper portion of the skirt 71.

Figure 16:
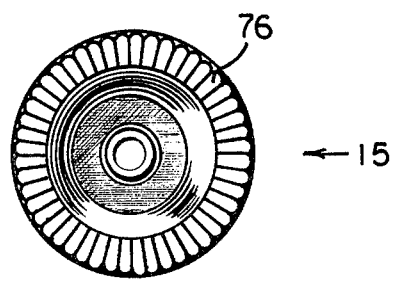
FIG. 16 is a top view of the syringe cartridge closure showing the closure ribs employed for machine torquing.
Figure 17:
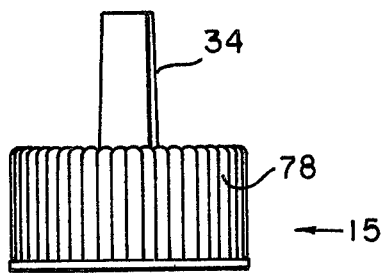
FIG. 17 is a front elevation of the syringe cartridge closure showing the knurled rim ribs for finger tightening.

As shown in FIG. 16, closure ribs 76 are provided above the seal portion 75 for machine torquing of the closure 15 onto the cartridge 11. As shown in FIG. 17, the closure 15 has knurled skirt ribs 78 to assist in hand tightening.

Figure 19:
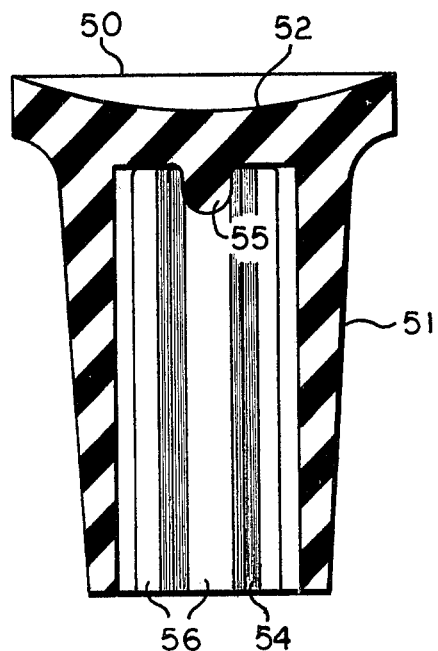
FIG. 19 is a transverse sectional view in enlarged scale of the leur tip cap.
Figure 20:
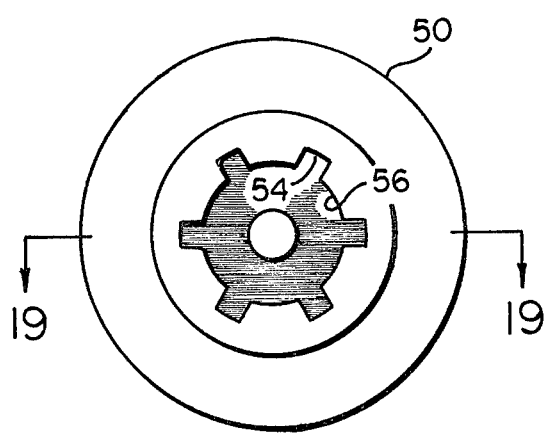
FIG. 20 is a bottom view of the leur tip cap showing the vent channels and the leur tip grip.

Finally, the leur tip cap 50 is shown in FIGS. 19 and 20. Turning specifically to FIG. 19, it will be seen that the leur tip cap 50 has a body portion 51, terminating in a thumb plate 52. In the interior portion of the body 51 means are provided to define vent channels 54, separating leur tip grips 56. A needle seal 55 is formed beneath the central portion of the thumb plate 52, and proportioned to fit into the dispensing end 46 of the needle upon reclosure. Another view of the vent channels end 54 and leur tip grip 56 appear in FIG. 20.

The Method

The method of filling, is primarily illustrated in FIG. 3. This presupposes, however, that a cartridge 11 has been provided with a plunger piston 14. As noted, the contents 12 are filled until a discrete level 32 has been reached, at a predetermined volume for displacement by the closure. The closure is then applied in such fashion that a small portion of the contents will flow into a trap so that when this position of the contents dry it will not be seen about the closure. The whole procedure is accomplished in such a fashion that zero head space remains between the contents 12 and the lower portion of the closure 15. The method for usage contemplates a leur tip cap which can be pressed downwardly and insert a dispensing needle through a diaphragm in the closure, and can be resealed by replacing the leur tip cap.

While the embodiment described is directed to a blood gas control medium, where other reagents are used which are not reactive to certain inert gases, zero head space is not essential. Then a small amount of gas, such as nitrogen, can be applied after filling. Then the closed cartridge does not require zero head space. A 0%–5% head space is then filled with an inert gas.

Although particular embodiments of the invention have been shown and described in full here, there is no intention to thereby limit the invention to the details of such embodiments. On the contrary, the intention is to cover all modifications, alternatives, embodiments, usages and equivalents of the subject invention as fall within the spirit and scope of the specification and the appended claims.

What is claimed is:

1. A syringe comprising, in combination,
a cylindrical cartridge having two open ends,
movable plunger means for closing one end of the cartridge,
a first closure means for the other end of the cartridge for displacement of product within the cartridge to achieve predetermined head space therein,
and a second closure means removably secured to said first closure means,
said second closure means having reseal means interacting with said first closure means to reseal with predetermined head space by displacing a portion of product in the first closure means.

2. In the syringe of claim 1,
tubular means interior of a central bore in an extension of said first closure means proportioned to penetrate a diaphragm in said first closure means and conduct product from said cartridge for dispensing.

3. In the syringe of claim 2,
said second closure means having product displacement means for displacing product from said tubular means to reclose said first closure means with zero head space.

4. In the syringe of claim 3,
said tubular means having a dispensing end and pointed end.

5. In the syringe of claim 1,
said second closure means having a vented portion to permit air to escape when reclosing.

6. A syringe cartridge comprising, in combination,
a cartridge of elongate cylindrical configuration having two open ends,
a plunger piston sealing the lower open end of said cartridge,
a syringe cartridge closure secured to the upper open end of the cartridge,
a leur tip having a dispensing end extending from said closure,
a leur tip cap proportioned to reclosably cover the dispensing end of the leur tip,
a leur tip bore centrally and longitudinally of the leur tip,
a diaphragm at the lower portion of said leur tip bore and closing the same to contents of the cartridge,
an inverted dome at the lower portion of the closure defining a predetermined head space relationship between the closure, cartridge, and contents,
the leur tip cap being proportioned for positioning over the leur tip.

7. In the cartridge of claim 6 above,
a hollow needle interior of the leur tip proportioned to penetrate the diaphragm upon depressing the leur tip cap.

8. In the syringe cartridge of claim 6 above,
said syringe cartridge closure having a contents displacement trap defined by its interior upper threaded portion, and the mating engagement with a threaded finish on the cartridge.

9. In the syringe cartridge of claim 6 above,
said leur tip cap having a vent means, whereby ambient air can be vented upon reclosing the leur tip cap.

10. In the syringe cartridge of claim 8 above,
said leur tip cap having a vent means, whereby ambient air can be vented upon reclosing the leur tip cap.

11. In the syringe cartridge of claim 7 above,
said leur tip cap having an interior needle seal proportioned to engage the upper end of the needle to assist in puncturing the diaphragm, and subsequently to assist in sealing the upper end of the needle.

12. In the syringe cartridge of claim 6 above,
a plunger shaft for engaging the plunger piston and forceably ejecting the contents of the cartridge through the hollow bore in the needle.

13. In the syringe cartridge of claim 6 above,
a second shaft piston proportioned for mating engagement with the plunger piston, and a shaft for engaging the shaft piston for forceably ejecting the contents of the cartridge through the hollow bore in the needle.

14. In the syringe cartridge of claim 7 above,
a plurality of needle seal rings interior of said leur tip needle bore, whereby the needle is supported for orientation upon penetration, and sealed from leakage of the contents.

15. A method for filling the contents of a syringe cartridge having predetermined head space between the contents and a plunger piston at one end of the cartridge and closure at its other end comprising the steps of,
positioning the cartridge in a vertical orientation,
closing off the open upper portion of the cartridge,
inserting contents into the cartridge while constantly venting the cartridge to permit normal escape of the air replaced by the contents,
terminating the fill at a level beneath the top of the cartridge of an air volume to be displaced upon closing the cartridge,
closing the cartridge with a syringe cartridge closure having a displacement dome and contents displacement trap,
and predetermining the fill so that a portion of the contents will pass outside of the cartridge and into the contents displacement trap of the cartridge and the reclosure means of the syringe closure top.

16. In the method of claim 15, the additional step of
opening the cartridge by depressing a pointed hollow needle held in a leur tip on the closure.

17. In the method of claim 16, the additional steps of
reclosing the closure at its leur tip by first expressing a bead of contents on the end of the leur tip,
and then applying a reclosure member to partially penetrate the leur tip.

18. In the method of claim 16,
predetermining the fill to permit a gas control to be applied atop the contents which remains in the cartridge after sealing.

* * * * *